United States Patent [19]

Mellul et al.

[11] Patent Number: 5,601,808
[45] Date of Patent: Feb. 11, 1997

[54] COSMETIC COMPOSITIONS FOR APPLICATION TO THE NAIL

[75] Inventors: Myriam Mellul, l'Hay-les-Roses; Valérie de la Poterie, le Chatelet en Brie, both of France

[73] Assignee: L'Oreal, Paris, France

[21] Appl. No.: 418,297

[22] Filed: Apr. 7, 1995

[30] Foreign Application Priority Data

Apr. 8, 1994 [FR] France ................................ 94 04202

[51] Int. Cl.$^6$ ................................................ A61K 7/04
[52] U.S. Cl. .............................................. 424/61; 424/401
[58] Field of Search ............................. 424/61, 401, 59

[56] References Cited

U.S. PATENT DOCUMENTS 4,649,045  3/1987  Gaske et al. ............................ 424/61
5,120,529  6/1992  Koch et al. ............................. 424/61

FOREIGN PATENT DOCUMENTS 0143480  6/1985  European Pat. Off. .
0391322  10/1990 European Pat. Off. .
0418469  3/1991  European Pat. Off. .
0504754  9/1992  European Pat. Off. .
0506300  9/1992  European Pat. Off. .
0593959  4/1994  European Pat. Off. .

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57] ABSTRACT

The present invention relates to a cosmetic composition for application to a nail, comprising as a film-forming agent an aqueous dispersion of particles of at least one polyurethane and of at least one radical-polymerization polymer containing carboxyl groups.

13 Claims, No Drawings

5,601,808

COSMETIC COMPOSITIONS FOR APPLICATION TO THE NAIL

The present invention relates to a cosmetic composition for application to a nail, comprising as a film-forming agent an aqueous dispersion of polymers.

A cosmetic composition of the nail varnish type, comprising as a film-forming agent an aqueous dispersion of polyurethane polymer or of polyurethane/acrylic/styrene copolymer, is known from European Patent Application EP 391 322 and from U.S. Pat. No. 5,120,529, the disclosures of which are hereby incorporated by reference. It was, however, observed that not all the aqueous dispersions mentioned in this document displayed a correct film-forming property, and that they hence did not enable a correct film of good quality to be obtained after spreading on the nail.

The object of the present invention is to provide aqueous dispersions which make it possible to obtain a varnish which can be readily applied to the nail and which yields a glassy film of good quality capable of being peeled off.

The present invention is thus drawn to a cosmetic composition for application to the nail, comprising as a film-forming agent an aqueous dispersion of particles of at least one polyurethane and of at least one radical-polymerization polymer containing carboxyl groups, wherein the polyurethane has a glass transition temperature (Tg) less than or equal to 30° C., and wherein, when the glass transition temperature of the polyurethane is greater than 0° C., the radical-polymerization polymer or mixture of radical-polymerization polymers has a minimum film-forming temperature (MFT) less than or equal to 30° C. and/or is present in an amount of from 5 to 60%, and wherein, when the glass transition temperature of the polyurethane is less than 0° C., the radical-polymerization polymer or mixture of radical-polymerization polymers is present in an amount of from 5 to 70%.

One advantage of the present invention is that it enables a hard and glassy homogeneous film to be obtained which adheres well to the nail, covering it perfectly while being capable of being peeled off.

Another advantage of the invention is that it enables a nail varnish containing little or no plasticizer or coalescing agent to be obtained.

Tg is understood in the description below to mean the glass transition temperature of the polyurethane.

MFT is understood in the description below to mean the minimum temperature at which film forms for the radical-polymerization polymer or mixture of radical-polymerization polymers.

Percentages are given by weight, i.e., by weight of the composition, except where otherwise stated.

The compositions according to the invention are characterized in that they comprise an aqueous dispersion of a mixture of particles of at least one polyurethane and of at least one radical-polymerization polymer containing carboxyl groups, it being necessary for the polyurethanes and radical-polymerization polymers to satisfy certain physicochemical conditions so that a suitable film forms from the aqueous dispersions on the nail.

It has, in effect, been noted that, depending on the type of polyurethane and/or radical-polymerization polymers employed, it either is or is not possible to obtain a correct film capable of being peeled off.

Only the compositions according to the invention enable a film displaying the necessary satisfactory qualities to be obtained on the nail.

In order to prepare the compositions according to the invention, an aqueous dispersion is prepared comprising particles of polyurethane and of radical-polymerization polymers containing carboxyl groups, for example by simply mixing an aqueous dispersion of polyurethane and an aqueous dispersion of radical-polymerization polymers, or by direct formation of a dispersion of a mixture of particles of polyurethane and of radical-polymerization polymers.

The aqueous dispersion of polyurethane can be, for example, an aqueous dispersion of anionic polyurethane, of polyester polyurethane and/or polyether polyurethane, alone or mixed, which can possess a dry matter content of 20–40%.

The polyurethane, or polyurethane mixture, employed must, however, possess a glass transition temperature (Tg) less than or equal to approximately 30° C.

The aqueous dispersion of radical-polymerization polymers may be chosen from all aqueous dispersions of acrylic, acrylic/styrene and vinyl polymers and/or copolymers, the dispersion preferably possessing a dry matter content of 30–50%. As is self-evident, the term "radical-polymerization polymer" as used herein means a polymer obtained by radical addition polymerization.

When the Tg of the polyurethane employed ranges from about 0° C. to 30° C., and preferably from 15° C. to 25° C., a radical-polymerization polymer or mixture of radical-polymerization polymers whose MFT is less than or equal to approximately 30° C. is chosen. In this case, a composition according to the invention containing 5–95% of dispersion of polyurethane and 5–95% of dispersion of radical-polymerization polymers can be prepared.

If it is not desired to employ a radical-polymerization polymer or mixture of radical-polymerization polymers whose MFT is less than or equal to 30° C., the content of the dispersion of radical-polymerization polymers in the composition may not exceed 60% by weight. Preferably, the content ranges from 35% to 60%.

When the Tg of the polyurethane is less than 0° C., and preferably from −15° C. to −5° C., the content of the dispersion of radical-polymerization polymers in the composition may not exceed 70% by weight, and preferably may not exceed 50% to 70% by weight.

It is preferable to prepare cosmetic compositions containing from 10 to 60% of polymer particles in the dispersed state.

Thickening agents, for example, hydroxyethyl cellulose or a cellulose derivative, a clay, a silicate or a silica derivative, a synthetic polymer such as a radical-polymerization polymer or an associative polymer of the polyurethane type, or a natural gum such as xanthan gum, may be added to the cosmetic composition in an amount of from 0.01 to 5%.

Standard additives such as spreading agents, wetting agents, dispersing agents, antifoams, preservatives, UV screening agents, active agents, moisturizers, alcohols, and inorganic or organic pigments alone or mixed, may also be added to the composition.

A cosmetic composition to be spread on the nail is thereby obtained. This composition preferably possesses a dry matter content of 10–60% which can comprise approximately 1–40% of dry matter of polyurethane and 1–50% of dry matter of radical-polymerization polymers.

The cosmetic composition thereby obtained spreads readily on the nail and, after drying, enables a hard and glassy film of good quality to be obtained on the nail, and which can be readily peeled off in a single piece.

This cosmetic composition can be used as a base for a solvent varnish, so as to permit the removal of make-up from the nail by simply peeling off without using a solvent. It can also, if it contains pigments, be used as a coloured varnish capable of being peeled off.

When it contains active agents, the composition can be employed as a treatment base for the nail. Among active agents which may be envisaged, vitamins, keratin and its hydrolysates, melanin, trace elements, glycerol and any other active agent capable of being envisaged by a person skilled in the art may be mentioned.

The invention is illustrated in greater detail in the examples which follow. The examples are not intended to be limiting, but merely ilustrative.

EXAMPLE 1

Several aqueous dispersions of particles of polyurethane having variable Tg values and of radical-polymerization polymers having variable MFT values, in variable proportions, were prepared by simply mixing a dispersion of polyurethane and a dispersion of radical-polymerization polymers and stirring for approximately 30 minutes at room temperature.

The dispersions thereby obtained were applied to the nail, and the film formed observed.

Polymers employed:

| | |
|---|---|
| polyurethane, Tg −10° C.: | dispersion of aliphatic anionic polyurethane IW/010.1 (UCB), containing 35% of dry matter |
| polyurethane, Tg 21° C.: | dispersion of aliphatic anionic polyurethane IW/019.1 (UCB), containing 35% of dry matter |
| polyurethane, Tg 36° C.: | dispersion of aliphatic anionic polyurethane IW/028.1 of (UCB), containing 35% of dry matter |
| radical-polymerization, MFT 12° C.: | dispersion of acrylic/styrene Joncryl 77 (Johnson), containing 46% of dry matter |
| radical-polymerization, MFT 35° C.: | dispersion of acrylic Luhydran A848S (BASF), containing 45% of dry matter |
| radical-polymerization, MFT 53° C.: | dispersion of acrylic/styrene Neocryl XK 63 (ICI), containing 44% of dry matter |
| radical-polymerization, MFT 86° C. | dispersion of acrylic/styrene Joncryl 90 (Johnson), containing 44% of dry matter |

The following results were obtained:

| | |
|---|---|
| dry extract: | dry matter content of the dispersion before application |
| %: | % of dispersion of polyurethane or of dispersion of radical-polymerization polymers in the mixture. |

| Polyurethane | | Radical-polymerization polymer | | dry extract | film |
|---|---|---|---|---|---|
| Tg (°C.) | % | MFT (°C.) | % | % | forming |
| −10 | 30 | 35 | 70 | 35 | yes |
| −10 | 20 | 86 | 80 | 35 | no |
| " | 30 | " | 70 | 35 | yes |
| " | 50 | " | 50 | 35 | yes |
| 21 | 20 | 12 | 80 | 35 | yes |
| " | 70 | " | 30 | 35 | yes |
| 21 | 20 | 35 | 80 | 35 | no |
| " | 40 | " | 60 | 35 | limiting* |
| " | 50 | " | 50 | 35 | yes |
| 21 | 20 | 53 | 80 | 35 | no |
| " | 40 | " | 60 | 35 | no |
| " | 50 | " | 50 | 35 | yes |
| 21 | 5 | 86 | 95 | 40 | no |
| " | 40 | " | 60 | 11 | no |
| " | 50 | " | 50 | 35 | yes |
| " | 60 | " | 40 | 16 | yes |
| 36 | 20 | 12 | 80 | 35 | no |
| " | 40 | " | 60 | 35 | no |
| " | 60 | " | 40 | 35 | no |
| " | 70 | " | 30 | 35 | no |
| 36 | 40 | 35 | 60 | 35 | no |
| " | 80 | " | 20 | 35 | no |
| 36 | 40 | 86 | 60 | 11 | no |
| " | 60 | " | 40 | 16 | no |
| " | 70 | " | 30 | 35 | no |
| " | 80 | " | 20 | 35 | no |
| " | 90 | " | 10 | 35 | no |

*"limiting" means film was not totally formed.

Hence it is seen that, depending on the Tg of the polyurethane employed, it is possible to obtain a correct film or no film at all.

When the Tg was greater than about 30° C., it was no longer possible to obtain good film formation on the nail.

When the Tg was below 30° C. but above 0° C., a satisfactory film was obtained when the MFT of the radical-polymerization polymer was less than or equal to about 30° C., or when the content of dispersion of polyurethane was greater than 40%. Furthermore, when the Tg of the polyurethane was below approximately 0° C., the content of aqueous dispersion of radical-polymerization polymers could not be more than 70%.

This example demonstrates the fact that not all mixtures of a dispersion of polyurethane with a dispersion of radical-polymerization polymer enable a correct film to be obtained, but that only the mixtures as defined by the invention permit perfect film formation and enable a suitable varnish to be obtained.

EXAMPLE 2

A nail varnish having the following composition was prepared:

| | |
|---|---|
| aqueous dispersion of aliphatic anionic polyurethane IW/019.1 (UCB), Tg <30° C., 35% of dry matter | 56 g |
| aqueous dispersion of anionic acrylic polymer NEOCRYL XK 90 (ICI), MFT: 18° C., dry matter: 44.3% | 19 g |
| polyurethane associative thickener Ser AD FX 1100 (Servo) | 0.8 g |
| spreading agent KF 355A (Shin Etsu) | 0.5 g |
| pigments | 1.5 g |
| propylene glycol | 0.2 g |
| water | 22.2 g |

All the constituents were mixed at room temperature, and the mixture was stirred for approximately 30 minutes so as to obtain a homogeneous composition.

A varnish was obtained which had a dry matter content of 28%, which could be spread easily on the nail and, after drying, enabled a glassy film of satisfactory hardness and appearance to be obtained.

This film was readily peeled off in a single piece.

EXAMPLE 3

A nail varnish having the following composition is prepared according to Example 2:

| | |
|---|---|
| aqueous dispersion of aliphatic polyester polyurethane Neorez R 981 (Zeneca Resins), Tg <30° C., dry matter: 33% | 59.4 g |
| aqueous dispersion of styrene/anionic acrylic copolymer Neocryl XK 62 (ICI), TMF: 30° C., dry matter: 42% | 20.0 g |
| polyurethane associative thickener Ser AD FX 1010 (Servo) | 1.25 g |
| spreading agent KF 355A (Shin Etsu) | 0.5 g |
| pigments | 1.5 g |
| water | 17.45 g |

A varnish was thereby obtained which had a dry matter content of 28%, which could be readily spread on the nail so as to obtain, after drying, a film of glassy appearance and satisfactory hardness, and which was readily peeled off.

EXAMPLE 4

A varnish was prepared identical to that of Example 3, but free from pigments. A colourless base was thereby obtained, which was readily applied to the nail.

After drying, this base was covered with a standard solvent varnish, and the said varnish was allowed to dry for a few minutes.

The make-up was then removed from the nail by peeling off the colourless base layer, which then carried off the solvent varnish and enabled a clean nail to be obtained.

What is claimed is:

1. A cosmetic composition for application to a nail, comprising as a film-forming agent an aqueous dispersion of particles of at least one polyurethane and of at least one radical-polymerization polymer containing carboxyl groups, wherein said at least one polyurethane has a glass transition temperature (Tg) less than or equal to 30° C., and wherein, when the Tg of said at least one polyurethane is greater than 0° C., said at least one radical-polymerization polymer has a minimum film-forming temperature (MFT) less than or equal to 30° C. and/or is present in the amount of from 5 to less than 60% by weight, and wherein, when the Tg of said at least one polyurethane is less than 0° C., said at least one radical-polymerization polymer is present in the amount of from 5 to 70% by weight.

2. A composition according to claim 1, wherein the Tg of said at least one polyurethane ranges from 15° C. to 25° C. and said at least one radical-polymerization polymer has an MFT less than or equal to 30° C. and/or is present in the amount of from 35 to less than 60% by weight.

3. A composition according to claim 1, wherein the Tg of said at least one polyurethane ranges from −15° C. to −5° C. and said at least one radical-polymerization polymer is present in the amount of from 50 to 70% by weight.

4. A composition according to claim 1, wherein said at least one radical-polymerization polymer containing carboxyl groups is an acrylic polymer or a vinyl polymer.

5. A composition according to claim 1, wherein said at least one polyurethane is an anionic polyurethane a polyester polyurethane, or a polyether polyurethane.

6. A process of cosmetic treatment of a nail, comprising the step of applying to the nail a composition according to claim 1.

7. A cosmetic composition for application to a nail, comprising as a film-forming agent an aqueous dispersion of particles of at least one polyurethane and of at least one radical-polymerization polymer containing carboxyl groups, wherein said at least one polyurethane has a glass transition temperature (Tg) less than or equal to 30° C., and wherein, when the Tg of said at least one polyurethane is greater than 0° C., said at least one radical-polymerization polymer has a minimum film-forming temperature (MFT) less than or equal to 30° C. and/or is present in the amount of from 5 to less than 60% by weight, and wherein, when the Tg of said at least one polyurethane is less than or equal to 0° C., said at least one radical-polymerization polymer is present in the amount of from 5 to 70% by weight.

8. A composition according to claim 7, wherein the Tg of said at least one polyurethane ranges from −30° C. to 0° C. and said at least one radical-polymerization polymer is present in the amount of from 5 to 70% by weight.

9. A composition according to claim 8, wherein the Tg of said at least one polyurethane ranges from −20° C. to 0° C. and said at least one radical-polymerization polymer is present in the amount of from 50 to 70% by weight.

10. A method of selecting at least one polyurethane and at least one radical-polymerization polymer as components of a film forming agent, comprising the steps of:

evaluating whether a polyurethane has a glass transition temperature (Tg) less than or equal to 30° C.;

selecting at least one polyurethane having said Tg; and combining said at least one polyurethane with at least one radical-polymerization polymer containing carboxyl groups, wherein, when the Tg of said at least one polyurethane is greater than 0° C., said at least one radical-polymerization polymer, combined with said at least one polyurethane, has a minimum film-forming temperature (MFT) less than or equal to 30° C., and/or combining said at least one polyurethane with at least one radical-polymerization polymer so that said at least one radical-polymerization polymer is present in an amount of from 5 to less than 60% by weight, and further, wherein when said at least one polyurethane has a Tg less than 0° C., combining said at least one radical-polymerization polymer with said at least one polyurethane so that said at least one radical-polymerization polymer is present in an amount of from 5 to 70% by weight.

11. A composition according to claim 1, wherein said at least one radical-polymerization polymer containing carboxyl groups is an acrylic\vinyl copolymer.

12. A composition according to claim 1, wherein said at least one radical-polymerization polymer containing carboxyl groups is a vinyl\styrene copolymer.

13. A composition according to claim 1, wherein said at least one radical-polymerization polymer containing carboxyl groups is an acrylic\vinyl\styrene copolymer.

* * * * *

UNITED STATES PATENT AND TRADEMARK OFFICE
CERTIFICATE OF CORRECTION

PATENT NO.: 5,601,808

DATED: February 11, 1997

INVENTOR(S): Myriam MELLUL et al.

It is certified that an error appears in the above-identified patent and that said Letters Patent is hereby corrected as shown below:

Claim 5, col. 6, line 2, after "anionic polyurethane", insert --,--.

Signed and Sealed this

Seventeenth Day of June, 1997

*Attest:*

BRUCE LEHMAN

*Attesting Officer*  *Commissioner of Patents and Trademarks*